(12) United States Patent
Hendriks et al.

(10) Patent No.: US 9,072,819 B2
(45) Date of Patent: Jul. 7, 2015

(54) REPAIR OF CARTILAGE TISSUE USING A MATRIX GEL CONTAINING CHONDROCYTES

(75) Inventors: Jeanine Anna Alphonse Hendriks, Amerongen (NL); Jens Uwe Riesle, Soest (NL)

(73) Assignee: CELLCOTEC B.V., Bilthoven (NL)

( * ) Notice: Subject to any disclaimer, the term of this patent is extended or adjusted under 35 U.S.C. 154(b) by 627 days.

(21) Appl. No.: 12/439,090

(22) PCT Filed: Aug. 31, 2007

(86) PCT No.: PCT/NL2007/050430
§ 371 (c)(1),
(2), (4) Date: Sep. 25, 2009

(87) PCT Pub. No.: WO2008/026928
PCT Pub. Date: Mar. 6, 2008

(65) Prior Publication Data
US 2010/0047316 A1    Feb. 25, 2010

(30) Foreign Application Priority Data

Aug. 31, 2006 (EP) .................................. 06076645

(51) Int. Cl.
| | | |
|---|---|---|
| *A61F 2/00* | (2006.01) | |
| *A61L 27/38* | (2006.01) | |
| *A61L 27/36* | (2006.01) | |
| *A61L 27/52* | (2006.01) | |
| *C12N 5/077* | (2010.01) | |

(52) U.S. Cl.
CPC .......... *A61L 27/3852* (2013.01); *A61L 27/3633* (2013.01); *A61L 27/3817* (2013.01); *A61L 27/52* (2013.01); *C12N 5/0655* (2013.01); *C12N 2501/00* (2013.01)

(58) Field of Classification Search
CPC ...... A61K 9/0024; A61K 35/32; A61L 27/14; A61L 27/20; A61L 27/22; A61L 27/24; A61L 27/44; A61L 27/54; A61L 31/16; A61L 2300/64

See application file for complete search history.

(56) References Cited

U.S. PATENT DOCUMENTS

| | | | |
|---|---|---|---|
| 4,846,835 A | | 7/1989 | Grande |
| 5,830,741 A | * | 11/1998 | Dwulet et al. ................. 435/220 |
| 2002/0022883 A1 | * | 2/2002 | Burg ................................. 623/8 |
| 2004/0134502 A1 | * | 7/2004 | Mizuno et al. ................. 128/898 |

FOREIGN PATENT DOCUMENTS

| | | |
|---|---|---|
| CA | 2254350 | 5/2000 |
| DE | 200 19 809 | 7/2001 |
| WO | WO-02/067856 | 9/2002 |
| WO | WO-02/078760 | 10/2002 |

OTHER PUBLICATIONS

Gagne, TA, K Chappell-Afonso, JL Johnson, JM McPherson, CA Oldham, RA Tubo, C Vaccaro, and GW Vasios. 2000. Enhanced Proliferation and Differentiation of Human Articular Chondrocytes when Seeded at Low Cell Densities in Alginate In Vitro. J. Orthopaedic Res.; 18: 882-890.*

Hoemann CD et al. Tissue engineering of cartilage using an injectable and adhesive chitosan-based cell-delivery vehicle. Osteoarthritis and Cartilage. 2005; 13: 318-329.*

International Search Report for PCT/NL2007/050430, mailed on Feb. 28, 2008, 5 pages.

Lin et al., "The Chondrocyte: Biology and Clinical Application," Tissue Eng. (2006) 12(7):1971-1984.

* cited by examiner

*Primary Examiner* — Carlos Azpuru
*Assistant Examiner* — David Browe
(74) *Attorney, Agent, or Firm* — Morrison & Foerster LLP

(57) ABSTRACT

The present invention relates in one aspect to the use of a matrix gel comprising chondrocytes or progenitor cells thereof in a density below that of natural cartilage as a cartilage repair implant wherein said cells exhibit increases production of extracellular matrix material.

8 Claims, 2 Drawing Sheets

REPAIR OF CARTILAGE TISSUE USING A MATRIX GEL CONTAINING CHONDROCYTES

CROSS-REFERENCE TO RELATED APPLICATIONS

This application is the national phase of PCT application PCT/NL2007/050430 having an international filing date of 31 Aug. 2007, which claims benefit of European patent application No. 06076645.8 filed 31 Aug. 2006. The contents of the above patent applications are incorporated by reference herein in their entirety.

FIELD OF THE INVENTION

The invention relates to the field of medical science. More in particular, the invention relates to technology aimed at repairing cartilage tissue in a patient in need thereof.

BACKGROUND OF THE INVENTION

Cartilage disorders are highly debilitating disorders including, for instance, articular cartilage trauma, meniscus injury, chondrogenesis disorders and arthritis. There are at present no optimal therapies available for treating these disorders. Cartilage tissue is neither innervated nor penetrated by the vascular or lymphatic systems and it is generally believed that due to this lack of a vasculature, damaged cartilage tissue does not receive sufficient or proper stimuli to elicit a repair response. Repair of arthritic joints thus requires orthopaedic surgery to replace the worn-out joints by a prosthesis or by a biological graft. Arthritis alone is an enormous medical and economic problem.

Hyaline cartilage, the most abundant form of cartilage, is glass smooth, glistening and bluish white in appearance, and of this form of cartilage articular cartilage is the most common. Articular cartilage covers the ends of long bones of synovial joints. It is characterized by a particular structural organization, consisting of chondrocytes embedded in an extracellular material, typically referred to as "cartilage matrix", which is an extracellular matrix rich in proteoglycans, collagen fibrils, other proteins, and water. Chondrocytes are the only cell type found in normal articular cartilage but contribute less then 2% of the wet weight in human healthy adult cartilaginous tissue.

The extracellular matrix of cartilage tissue consists predominantly of cartilage specific proteoglycan molecules with highly negatively charged sulphated glycosaminoglycan (GAG) side chains, as well as type II collagen fibrils. The GAG side chains are able to bind water molecules, thereby sequestering water and generating an internal swelling pressure within the cartilage matrix. These hydrogel-like properties are essential for the interstitial fluid flow patterns observed inside the matrix during functional loading of cartilage, at which point water is forced out of the tissue to an amount that allows the negatively charged GAG chains to repel each other. Upon release of the compressive load, water is imbibed back into the tissue matrix. The collagenous network, together with water bound GAG, enables articular cartilage to withstand large compressive loads which gives the tissue its unique function in synovial joints: smooth and pain-free articulation, spreading of the applied load onto the subchondral bone and absorbing mechanical shocks.

In normal cartilaginous tissue, proteoglycans are slowly but continuously turned over, the degraded molecules are released from the cartilage and are replaced by newly synthesized components. It is the coordinate control of synthesis and degradation of the matrix components by the chondrocytes that maintain normal cartilage.

Current approaches for cartilage repair rely on removal of tissue debris, access to the wound healing system of bone by penetrating the subchondral bone plate, and tissue transplantation and cell based therapies. Current clinical therapies are limited to autologous cell based therapies, such as autologous chondrocytes implantation (ACI) and mosaicplasty (also known as autologous osteochondral grafts). Due to severe drawbacks, both therapies can currently only address a limited share of the cartilage repair market.

For mosaicplasty, a major disadvantage is the limitation to small defects due to limited availability of donor tissue for transplantation. For ACI, drawbacks include the necessity to perform two surgical operations, one for extracting the autologous chondrocytes and preparation of the transplant site, and another for implantation of the in vitro expanded chondrocytes. Apart from the fact that high costs are involved, the ACI process is long since cartilage cells de-differentiate, or lose their phenotype, upon cell expansion. Hence, several months are needed following the surgical extraction procedure for the cells to regain their original phenotype. Only then true cartilage repair can commence.

Recently, a second generation ACI has been developed involving autologous chondrocytes in a biomaterial matrix. This technique solves some of the problems of ACI, particularly the long and open surgical procedure that was required in ACI. However, three important drawbacks remain: two surgical procedures have to be carried out, involving high costs and long rehabilitation.

Accordingly, there is a need for further improvements in the field of repair of tissue defects, in particular for defects which are not, or not sufficiently repaired in a spontaneous fashion.

SUMMARY OF THE INVENTION

The present invention provides a method for repairing cartilage tissue using cells, preferably autologous cells, that can be harvested during the same surgical procedure as the one carried out for repairing the defective tissue. Hence, only one surgical procedure needs to be carried out, involving back-to-back extraction, isolation and implantation of autologous cells. The method is particularly useful for chondrocytes. The isolation method used to obtain these cells is quick, within 1 minute to 2 hours, and results in sufficient cells for achieving effective cartilage repair when executed in accordance with the invention. Also, the invention does not require any in vitro culturing of cells during which the cells might de-differentiate, and the method is therefore much more time effective than previous methods.

In a first aspect, the present invention provides the use of a matrix gel comprising chondrocytes as a cartilage repair implant, wherein said chondrocytes have been obtained from a cartilage sample by an isolation procedure involving digestive treatment wherein upon isolation said chondrocytes are mixed with a matrix gel material to obtain the said matrix gel comprising chondrocytes as a (preferably homogeneous) dilution of said isolate, and wherein said chondrocytes in said matrix gel exhibit increased production of extracellular matrix material.

In a preferred embodiment, the matrix gel comprising chondrocytes comprises chondrons and wherein the averaged number of chondrocytes per chondron is lower than in said cartilage sample.

In another preferred embodiment, the matrix gel comprising chondrocytes is essentially free of chondrons.

In another preferred embodiment, the matrix gel comprises a fibrin glue, hyaluronic acid, alginate, propylene fumarate-co-ethylene glycol hydrogel, hydrogypropyl methylcellulose hydrogel, collagen mimetic peptide, chitosan, collagen, gelatin, (ethylene glycol)-co-poly(lactic acid)hydrogel, agarose, Pluronic™ F-127, or combinations thereof. More preferably, said matrix gel is essentially composed of said matrix gel material.

In another preferred embodiment said chondrocytes are autologous chondrocytes and the cell density in said matrix gel is preferably 0.8 to 40,000 times lower, more preferably 8 to 5,000 times lower than that of the source of the autologous chondrocytes.

In still another preferred embodiment said autologous chondrocytes are obtained by providing a sample of a suitable autologous source and separating said chondrocytes from said sample by electrophoretic separation. The sample is preferably a cartilage sample In yet a further preferred embodiment the sample is subjected to digestion prior to said electrophoretic separation. The digestion is preferably performed in a digestion solution comprising at least one enzyme selected from the group consisting of collagenase, dispase, trypsin, hyaluronidase, chondroitinase ABC, elastase, heparitinase and alpha-chymotrypsin.

In still a further preferred embodiment, said autologous source is articular cartilage.

In still a further preferred embodiment, said matrix gel comprising said chondrocytes is used for the manufacture of a medicament for treating a cartilage-related disorder.

In still a further preferred embodiment, said disorder is articular cartilage trauma, meniscus injury, chondrogenesis disorders or arthritis.

In another aspect, the present invention provides a method for repairing a cartilage defect in a mammal in need thereof comprising the steps of:
a) providing a sample of a suitable autologous source of chondrocytes;
b) isolating said chondrocytes from said sample;
c) mixing the thus isolated chondrocytes with a matrix gel material to obtain a diluted isolate wherein said cells exhibit increases production of extracellular matrix material;
d) optionally loading said matrix gel comprising said chondrocytes in or on a scaffold, and
e) implanting said matrix gel or said loaded scaffold in a cartilage defect.

In aspects of the present invention the term "mammal" includes humans.

In a preferred embodiment of said method, the sample of a suitable autologous source is obtained from the body part comprising the site of the defect.

In another preferred embodiment of said method, said autologous source is a source of articular cartilage.

In yet another preferred embodiment of said method, said electrophoretic separation is performed by
a) mincing said sample to fragments;
b) optionally subjecting said fragments to enzymatic digestion;
c) submerging said optionally digested fragments in an electrophoresis gel;
d) subjecting said submerged fragments to electrophoresis conditions, and
e) isolating said chondrocytes from the electrophoresis buffer.

Preferably, the matrix gel material is a biocompatible matrix gel material, preferably selected from the group consisting of fibrin gel, hyaluronic acid, alginate, propylene fumarate-co-ethlene glycol hydrogel, hydrogypropyl methylcellulose hydrogel, collagen mimetic peptide, chitosan, collagen, gelatin, (ethylene glycol)-co-poly(lactic acid)hydrogel, agarose, Pluronic™ F-127, copolymers of poly(ethylene glycol)-terephthalate (PEGT) and poly(butylene terephthalate) (PBT), and combinations thereof.

In a preferred embodiment of a method or the invention, the cells are mixed with said matrix gel material to result in a cell density corresponding to a dilution of 0.8 to 40,000 times relative to that of the autologous source, more preferably of 8 to 5,000 relative to that of the autologous source. The mixture is preferably homogeneous as explained elsewhere herein.

In another preferred embodiment of a method or the invention, the increased production of extracellular matrix material is exhibited through an increase in the GAG/DNA ratio within said matrix gel. Thus, while the amount of DNA per volume of matrix gel material decreases with increasing dilution rate, the amount of GAG measured after an period of 3 weeks increased or stayed the same. It is to be understood that this increase in the GAG/DNA ratio will also occur when the diluted chondrocyte matrix gel is implanted in the cartilage defect, so that the measurement of the increased production of extracellular matrix material is best measured in parallel experiments or pre-clinical tests.

In yet another aspect, the present invention relates to a matrix gel comprising autologous chondrocytes at a density below that at which the chondrocytes are present in the cartilage from which the chondrocytes were obtained when produced by the method according to the present invention as described in detail above.

In yet another aspect, the present invention relates to a scaffold comprising the matrix gel of the present invention as described above.

In yet another aspect, the present invention relates to a method for electrophoretic separation of cells from a tissue the method comprising:
a) mincing a tissue to prepare fragments of said tissue, optionally pre-incubating said fragments in a digestion solution;
b) submerging the optionally pre-digested tissue fragments in a suitably small amount of a suitable electrophoresis gel material;
c) subjecting the electrophoresis gel thus loaded with the optionally pre-digested tissue fragments to electrophoresis conditions, whereby the cells are caused to migrate out of electrophoresis gel into a suitable aqueous solution surrounding the electrophoresis gel.

In a preferred embodiment of such a method, the tissue is cartilage and the cells are chondrocytes.

Figure 1A:
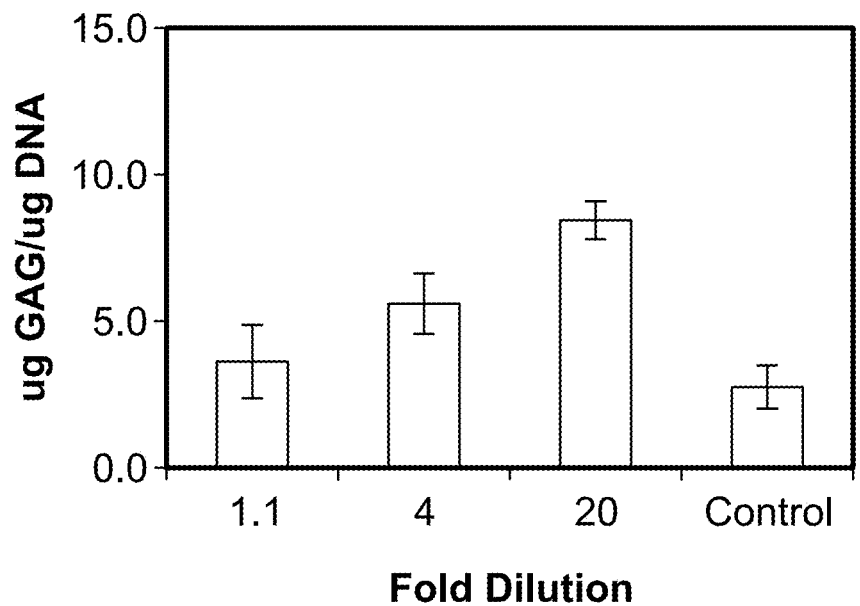
FIGS. 1A-B show the result of the experiment as described in the Example and indicate the effect of dilution on cartilage matrix metabolism (production) of primary chondrocytes at the end of the 3 week cultivation period, wherein the production of glycosamineglycan (mg glycosaminoglycan/mg DNA) is indicated by the height of the bar with standard deviations indicated.

image of safraninO stained sections of the pellets. Detailed pictures are taken either at the border of the pellet or in the middle.

DETAILED DESCRIPTION OF THE INVENTION

Culturing cartilage from primary chondrocytes has been found to be highly problematic due to the fact that primary cartilage-derived cell cultures undergo dedifferentiation, acquire fibroblastic features, and lose most of the characteristics of mature chondrocytes. It is believed that this phenomenon is due mainly to the loss in culture of the close matrix-cell interrelationship typical of cartilage tissue, which is a vital element of cartilage formation and homeostasis. The sustenance of the differentiated state of the chondrocytes is thus dependent on close cell-matrix interactions, such that releasing the cells from their cartilaginous environment results in a rapid loss of their phenotypic morphology and function.

The present invention now provides a method for electrophoretic separation of cells from a tissue. This method may very suitably be used to isolate chondrocytes from cartilage.

A method for electrophoretic separation of cells from a tissue comprises mincing the tissue to prepare fragments of the tissue, preferably approximately 0.5 to 2 mm in diameter, more preferably about 1 mm. Mincing may be performed by any suitable method, for instance using scissors, a razor blade, a scalpel, straining through a steel or nylon mesh screen or sieve, or disaggregating it through a needle.

The fragments are then optionally pre-incubated in a digestion solution. The digestion solution comprises one or more enzymes. Suitable enzymes are for instance collagenase, dispase, trypsin, hyaluronidase, chondroitinase ABC, elastase, heparitinase, alpha-chymotrypsin, etc. The type of enzyme will depend on the type of tissue used. A suitable amount of enzyme is for instance 0.15-2 wt. %, based on the weight of the digestion solution.

The digestion solution may further comprise buffering agents which help to maintain the pH in the range which approximates physiological conditions. They are preferably present at concentration ranging from about 1 mM to about 100 mM. Suitable buffering agents for use in the present invention include both organic and inorganic acids and salts thereof such as citrate, succinate, tartrate, fumarate, gluconate, oxalate, lactate, acetate phosphate and borate buffers. Additionally, there may be mentioned, histidine, glycine and urea buffers and buffers such as Tris, MOPS and HEPES.

The digestion solution may further comprise such compounds as: chelating agents, e.g. diethylenetriaminepentacetic acid (DTPA), ethylenediaminetetraacetic acid (EDTA, e.g. as Versene™), ethylene bis(oxyethylenenitrolo)tetraacetic acid (EGTA); reducing agents, such as dithiotreitol, dithioerythritol, β-mercaptoethanol, glutathione, thioredoxine, cysteine, etc.; ions necessary for activation of the enzyme such as $CaCl_2$, $MgCl_2$, NaCl and/or KCl; and/or organic solvents or lipid/membrane modifying agents such as dimethyl sulfoxide (DMSO); nonionic detergents such as triton X-100; and/or osmoprotectants such as sucrose.

The pre-digestion is not always necessary, for instance in the case of electrophoretic separation of cells from a tissue (in particular chondrocytes form cartilage), the tissue may be sufficiently minced, and the cells may then be caused to migrate out of the tissue by electrophoresis.

The optionally pre-digested tissue fragments are then subjected to electrophoresis. To this end, they are preferably submerged in the lowest possible volume of a suitable electrophoresis gel. Examples of suitable electrophoresis gels are for instance electrophoresis gels based on agarose, dextran, polyethylene glycol, Ficoll, Percoll, polyacrylamide, etc., or a combination thereof.

The electrophoresis itself may be carried out under conditions well known in the art, whereby a voltage is applied to the electrophoresis gel creating an electric field causing the cells in the electrophoresis gel to migrate out of electrophoresis gel into a suitable aqueous solvent surrounding the electrophoresis gel, i.e. the electrophoresis buffer.

Another isolation procedure is one where the tissue, in particular the cartilage, is subjected to rapid digestion (in the case of cartilage with collagenase type II) for a period of time compatible with intra-operative or single-surgery therapy or treatment, such that the cells can be mixed with the gel and the gel comprising the cells can be implanted in the patient, preferably the same patient from which the cells were extracted. A suitable digestion period is for instance as short as 1 mm to 2 hrs, preferably 5 min to 1 hr, most preferably 10-30 min, whereupon the cells are isolated from the tissue matrix. It was found that in the case of cartilage, very rapid isolation of the chondrocytes is possible. This then allows for (preferably autologous) tissue replacement as a form of intra-operative or single surgery therapy.

In a preferred embodiment, particularly in the case of rapid digestion, the tissue sample is subjected to a treatment to increase extracellular matrix permeability prior to subjecting it to the digestion enzyme. It is contemplated that one of the factors determining the efficiency of the isolation of cells from the tissue sample, is the access of the digestion enzyme to the cells and extracellular matrix in the sample. The permeability of cartilage is determined by chemical and mechanical factors, water and proteoglycan interactions. It is preferred that the treatment to increase extracellular matrix permeability, particularly for cartilage tissue, comprises increasing repulsive forces between glycosaminoglycans present in the extracellular matrix. In a preferred embodiment, this treatment comprises contacting the tissue sample to an acid, a base, dimethyl sulfoxide (DMSO), cathepsin, glycerol, or cations, or any other agent which may increase the Donan osmotic pressure of the extracellular matrix or cause the extracellular matrix to swell, prior to subjecting it to the digestion enzyme.

Suitable examples of cations include $Na^+$, $K^+$, $NH_4^+$, $Pb^{2+}$, $Mg^{2+}$, $Zn^{2+}$, $Fe^{2+}$, $Cd^{2+}$, and $Cu^{2+}$. These may for instance be introduced in the form of their chloride salts, preferably in a concentration between 10 mM and 2 M. A suitable acid is for instance hydrochloric acid, preferably in a concentration of 10-100 mM, resulting in a decrease of the pH of the extracellular matrix. Dimethylsulfoxide (DMSO) and glycerol may be used in a concentration between 5 and 30% v/v. Other suitable agents for this step include disodium ethylenediaminetetraacetate (EDTA) or ethyleneglycolbis (β-aminoethyl ether) N,N'-tetraacetic acid (EGTA), both preferably used in a concentration of 0.01-0.1 M) or citrate in Tris buffer, pH 5.8 and 7.4, at 4° and 37°. After the permeability of the tissue is increased, the tissue sample may be washed with for instance phosphate buffered saline before subjecting it to a digestion enzyme.

The step of increasing permeability preferably lasts from 1 minute up to no more than 1 hour, preferably maintaining the total isolation time of the cells to be within the 2 hour range. It is preferably performed at a temperature between 17° C. and 37° C.

The above-described isolation procedures are an aspect of the present invention, and may be used broadly for the isolation of cells from tissues. In particular it can be employed for the isolation of chondrocytes from cartilage, preferably articular cartilage. In a preferred embodiment, the chondrocytes are isolated from cartilage in a body part, such as a joint, comprising a defect. The site of isolation may be the site of the defect to be repaired itself, or be in its vicinity. The chondrocytes thus obtained are not de-differentiated and can be used in other aspects of the present invention.

In the context of the invention, chondrocytes which are not de-differentiated are considered to substantially not show the elongated morphology de-differentiated chondrocytes typically do. In addition, it is noted that de-differentiated chondrocytes often only produce collagen type I, and no collagen type II, and accordingly have a collagen II/I ratio of less then 1. As mentioned, in accordance with the invention de-differentiation of chondrocytes is largely avoided.

Aspects of the present invention are partly based on the insight that the simple dilution of primary chondrocytes in a gel matrix results in an increase in the rate of matrix production on a per-cell basis.

Without whishing to be bound by theory, one hypothesis is that this may be due to the release of the chondrocytes from the chondron, the microanatomical unit composed of a chondrocyte and its pericellular microenvironment (PCME), including the pericellular matrix and capsule. Chondrons usually contain more than one chondrocyte. The tissue-averaged number of chondrocytes per chondron in, for instance, the knee, is typically 2.0 throughout the knee, while the tissue-averaged number of chondrons per unit volume is around $5 \times 10^6$ per $cm^3$. Thus, the tissue-averaged number of chondrocytes per unit volume in the knee articular cartilage is about $10 \times 10^6$ chondrocytes per $cm^3$ at the indicated ratio of 2.0 chondrocytes per chondron. In the chondron, the chondrocytes are close together. Thus, it is envisaged that the chondrocyte in the matrix gel is essentially free from the chondron environment, which is the direct result form the isolation procedure, and that the chondrocytes are not in close contact, but spaced apart by a gel. It is further envisaged that after the chondrocytes have been applied to the gel, chondrons may reform.

A typical cultivation method for chondrocytes is micromass cultivation. Micromass cultivation is a type of cultivation wherein cells from a suspension are spun down by centrifugation and cultivated in the form of the resulting pellet, adhered together.

The present method comprises the dilution of isolated and concentrated cells with a gel material, such that the individual cells are not adhered together, but spaced apart.

In one embodiment, primary (freshly isolated) chondrocytes may be isolated, concentrated and diluted with a gel-forming material. The gel forming material (also called gel material herein, e.g. agarose) is preferably mixed in non-solidified form with the cells by thorough but gentle resuspension of the concentrated cells with a composition, such as a solution or a suspension of the gel-forming material and the material is then allowed to form the gel. For instance, the mixture of cells in the composition of the gel-forming material before gelling may be put on ice in the case of an agarose slurry, for a short duration of time. Upon gelling, the gel cultures may then be cultured under standard conditions in order to allow the cells to form extracellular material, or the gel cultures may be implanted directly for the tissue repair purpose.

The present method comprises the dilution of isolated and subsequently concentrated cells, preferably chondrocytes with a gel material, such that the individual chondrocytes are not adhered together, but spaced apart. Over a significant range, it was found that the further spaced-apart these cells in such a gel were, the higher the production of GAG per cell.

Thus, the present invention envisions to use of cells growing at a distance form each other, or stably spaced apart, e.g. by being separated be the rigid solidified gel through which they cannot move, for the acceleration of the formation of extracellular material, in particular GAG, or to induce production of cartilage extracellular matrix and/or cartilage tissue. Thus, the present invention envisages the use of the gel for a particular beneficial purpose of improving the conditions of cartilage production from primary chondrocytes.

Very suitably, the isolated chondrocytes may be mixed with a matrix gel material, so that they become suspended in said matrix gel material to a cell density that is lower than that of the concentrated isolate. For instance, if the original chondrocyte density in the concentrated isolate is $80 \times 10^6$/ml, than the isolated chondrocyte are suspended in an appropriate volume to result in a chondrocyte density of less than $70 \times 10^6$/ml, for instance 60, 50, 40, 30, 20, 10, 5, 4, 3, 2, 1, 0.5, 0.4, 0.3, 0.2, 0.1, 0.05, 0.02, 0.01, 0.005, or $0.002 \times 10^6$/ml. In one preferred embodiment, an amount of matrix gel material is provided to result in a separation of the chondrocytes close to their original density in tissue, which is about $10 \times 10^6$/ml.

Preferably the cells are suspended homogeneously in said matrix gel material so that the dilution results in the cells being positioned at even distances from each other.

The clinical concentration of the cells (i.e. the density of the gel-comprising-chondrocytes implant) will preferably be in the range of $0.002$-$1.0 \times 10^6$ cells/ml, more preferably in the range of $0.02$-$0.6 \times 10^6$ cells/ml.

Clinically, the method comprises the taking of a biopsy of cartilage by the surgeon, isolating chondrocytes from the cartilage according to method, preferably by a method as described herein optionally washing the cells, concentrating (e.g. by filtration or centrifugation or any other suitable method, preferably by filtration the cells through a cell strainer) to remove any isolation fluid and redundant cartilage tissue components, dilution the thus contracted cells with the composition of gel-forming material, gelling the composition and implanting the gel comprising the chondrocytes in the patient.

As a suitable matrix gel material any matrix gel material that is not cytotoxic can be used. Preferably, the matrix gel material is biocompatible, meaning that the material is accepted by a tissue surface. The broad term biocompatible includes also nontoxic, noncarcinogenic, chemically inert, and stable in the living body. Suitable biocompatible materials include fibrin glue, hyaluronic acid, alginate, propylene fumarate-co-ethylene glycol hydrogel, hydrogypropyl methylcellulose hydrogel, collagen mimetic peptide, chitosan, collagen, gelatin, (ethylene glycol)-co-poly(lactic acid)hydrogel, agarose, Pluronic™ F-127, copolymers of poly(ethylene glycol)-terephthalate (PEGT) and poly(butylene terephthalate) (PBT) (such as disclosed in e.g. WO 2006/085747, the contents of which are incorporated herein by reference), or combinations thereof.

The term "extracellular matrix", abbreviated "ECM", refers to the complex structural material that is produced by cells in mammalian tissues, particularly cells of connective tissue, for instance such cells as fibroblasts, osteoblasts, chondrocytes, epithelial cells, smooth muscle cells, adipocytes, and mesenchymal cells, and which material in vivo surrounds and supports those cells. Typically, the ECM is composed of fibres embedded in what is commonly referred to as 'ground substance'. The fibers are composed of structural proteins, generally collagen and/or elastin. The ground substance is composed of proteoglycans (or mucopolysaccharides).

In aspects of the present invention, the matrix gel material may comprise one of more of the components proteoglycans, GAGs, fibers and functional proteins.

The fibers of the matrix gel may be any fiber. Preferred are elastin and/or collagen fibers. Highly preferred are collagen fibers. Particularly suitable collagens are fibril-forming collagens. Type I collagen, type II collagen, type III collagen, type IV collagen or type X collagen are particularly preferred. Most preferred is type II collagen. A suitable amount of collagen is for instance 1-90 wt %, based on the total weight of the gel matrix material.

In aspects of the invention, the matrix gel material preferably comprises at least one proteoglycan. The proteoglycan is preferably composed of a core protein with pending glycosaminoglycan (GAG) molecules. Suitable GAGs are for instance hyaluronic acid, chondroitin-4-sulfate, chondroitin-6-sulphate, dermatan sulphate, heparin sulphate, heparin sulphate, and keratan sulphate. The GAGs are preferably linked to the core protein via a trisaccharide linker (e.g. a Gal-GalXyl-linker). Exemplary proteoglycans are decorin, biglycan, versican and aggrecan. The proteoglycans may optionally be interconnected by hyaluronic acid molecules. Alternatively, multiple proteoglycans may be attached to a single hyaluronic acid backbone. In both cases the matrix gel forms a polymer network or hydrogel capable of holding water. A suitable amount of proteoglycan is for instance 1-90 wt %, based on the total weight of the gel matrix material.

The matrix gel material may further comprise one or more functionality-providing proteins such as: glycoproteins such as laminin, entactin, tenascin fibrillin or fibronectin, for improving structural integrity of the network and for the attachment of cells to the matrix gel; osteocalcin (Gla protein), as a protein that binds calcium during mineralization; osteonectin, which serves a bridging function between collagen and mineral component; and sialoproteins, such as bone sialoprotein (BSP), osteopontin (OPN), dentin matrix protein-1 (DMP1), dentin sialophosphoprotein (DSPP) and matrix extracellular phosphoglycoprotein (MEPE). A suitable amount of protein is for instance 1-90 wt %, based on the total weight of the gel matrix material.

The matrix gel may further comprise cytokines and growth factors. Suitable cytokines and growth factors include osteoprotegerin (OPG), epidermal growth factor (EGF), fibroblast growth factors (bFGF, FGF-1, and FGF-2), interferon-α (IFN-α), interleukins (IL-1, IL-4, IL-6, IL-10, and IL-11), platelet-derived growth factor (PDGF), transforming growth factors (TGF-α and TGF-β), tumor necrosis factors (TNFs), insulin-like growth factors (IGF-I and IGF-II), osteoclast differentiation factor (ODF, also known as OPGL [osteoprotegerin ligand], RANKL [receptor activator of NFB ligand], TRANCE [TNF-related activation-induced cytokine]), and macrophage colony-stimulating factor (M-CSF). Preferred growth factors include BMP, IGF, PTH and PDGF. The matrix gel material in aspects of the present invention can be a natural or artificial material (e.g. a proteinaceous or peptide hydrogel). Suitable amounts of these cytokines and growth factors are known to those skilled in the art, and can be varied according to need.

Once the cells are mixed with the matrix gel material, a material is obtained that may serve the function of a repair material. For simplicity, this material may be referred to as the (autologous) chondrocyte implant. This (autologous) chondrocyte implant may be associated with a scaffold in order to provide even more structural integrity to the implant. Both the (autologous) chondrocyte implant as well as the loaded scaffold are aspects of the present invention. It will be understood that this implant need not necessarily be implanted by methods that require long and open surgical procedures. Instead, it can be prepared and implanted by minimally invasive techniques such as endoscopic methods.

The matrix material may suitably be prepared by mixing the selected components in an aqueous medium, preferably water, and optionally adding components to allow the components to acquire their 3D-orientation or to allow self-assembly of the components into a 3D-hydrogel.

The aqueous medium in which the matrix-gel components are combined or added may further comprise electrolytes, e.g. ions such as $CaCl_2$, $MgCl_2$, NaCl and/or KCl; nutrients; buffering agents which help to maintain the pH in the range which approximates physiological conditions as described above for the digestion solution; osmoprotectants, and other excipients.

It will be appreciated that the matrix material may be prepared in advance and stored under proper conditions ready for use, which is of great benefit to surgical procedures that include i) the autologous extraction of chondrocytes, ii) the isolation of the chondrocytes and iii) the preparation of the (autologous) chondrocyte implant according to the invention. The preparation of the (autologous) chondrocyte implant will then require no more time than the isolation of the chondrocytes from the patient in need of the surgical treatment. Once prepared it is preferred that the (autologous) chondrocyte implant or alternatively, the loaded scaffold, is implanted immediately in the optionally prepared implantation site.

The invention will now be further elucidated by the following, non-restrictive examples.

EXAMPLES

Materials & Methods

Bovine Primary Chondrocytes

BPCs were used in experiments immediately after isolation. For isolation of these cells, full thickness articular cartilage was dissected from the patellar femoral groove of adult bovine. Dissected cartilage was minced and was incubated for 20-22 hrs in collagenase type II solution containing 0.15% collagenase (Worthington), Dulbecco's modified Eagle's medium (Gibco) supplemented with penicillin (100 U/ml) and streptomycin (100 µg/ml). The suspension, which is essentially free of chondrons, was filtered through a 100 µm mesh nylon filter (cell strainer Nucleon) and chondrocytes were washed 2 times with phosphate buffered saline (PBS) supplemented with penicillin (100 U/ml) and streptomycin (100 µg/ml).

Micromass Culture

Micromass cultivation is a type of cultivation wherein cells from a suspension are spun down by centrifugation and cultivated in the form of the resulting pellet, adhered together.

The present method comprises the dilution of that micromass with a gel material, such that the individual chondrocytes are not adhered together, but spaced apart.

Primary (freshly isolated) BPCs chondrocytes were isolated separately as pellets of approximately 500.000 cells/pellet, and were diluted with 1% agarose by thorough but gentle resuspension of the pellet with a melt of 1% low melting agarose according to the following scheme.

A total of 6 groups and one control was prepared. For groups A, B and C the amount of agarose added to the pellet (was 500.000 cells/pellet) was 6 µl, 21.8 µl and 106 µl in order to prepare dilutions of the isolated pellet of 1.1×, 4.0× and 19.8×, respectively. Thus keeping the amount of cells constant and increasing the volume of the gel. For group D, E and F the volume of the pellet was 10.6 µl and the amount of cells/pellet for 2.0×, 4.0× and 19.8× dilution respectively 500.000, 250.000 and 50.000. Thus keeping the gel volume constant, while varying the amount of cells.

TABLE 1

Dilution scheme indicating at which dilutions the cultivation of the primary chondrocytes in micromass-culture was started and the amounts of DNA and matrix material (sulphated glycosaminoglycans) produced in a culture period of 3 weeks.

| Group | Concentration Primary chondrocytes $*10^6$/ml | Fold dilution (x) | Total GAG ug | total DNA ug | GAG/DNA ug/ug |
|---|---|---|---|---|---|
| A | 83 | 1.1 | 31.0 ± 9.2 | 8.8 ± 1.8 | 3.5 ± 1.3 |
| B | 23 | 4 | 40.9 ± 2.0 | 7.3 ± 1.4 | 5.6 ± 1.1 |
| C | 4.7 | 20 | 45.8 ± 1.9 | 5.4 ± 0.3 | 8.4 ± 0.6 |
| D | 47 | 2 | 41.7 ± 2.6 | 7.3 ± 1.3 | 5.7 ± 1.1 |
| E | 23 | 4 | 46.0 ± 2.5 | 5.0 ± 1.2 | 9.2 ± 2.3 |
| F | 4.7 | 20 | 38.3 ± 2.9 | 4.3 ± 2.3 | 8.9 ± 4.8 |
| control | 93 | — | 26.5 ± 6.0 | 8.8 ± 1.2 | 3.0 ± 0.8 |

Upon dilution, the mixtures were put on ice for 1 minute. Agarose/cell constructs were cultured under standard conditions in 3 ml of CM1 in a polypropylene Falcon centrifuge tube for 3 weeks and medium was refreshed every 3-5 days. Each group consisting of 9 gel-mixture cultures was further individually investigated for histology, in situ hybridization, immunohistochemistry or quantitative biochemical analysis.

Histology

Micromass cultures were fixed with 1.5% glutaraldehyde in cacodylate buffer (0.14 M/pH 7.2-7.4). Samples were washed in PBS, dehydrated and embedded in Paraffin. Sections (5 μm) were cut with a microtome and stained for sulphated Glycosaminoglycans (GAG) with safraninO and counterstained with haematoxyline (Gill nr3) and fast green to visualize nuclei and cytoplasm respectively.

Immunohistochemistry

Micromass cultures were embedded in OCT compound (Tissue-Tek) and immediately frozen at –80° C. for immunostaining. Sections (5 μm) were cut with a cryotome and fixed with acetone for 10 min. Cryo-sections were stained overnight at 4° C. for Type II collagen (1:100, DSHB # II-II6B3). Blocking was done with 10% human serum and, as a secondary antibody, goat anti-mouse (1:100, DAKO) was used. Staining was visualized with 3, 3 diaminobenzidine (DAB)-solution (DAKO) for 10-20 minutes. Specificity of Human specific MHC Class I antibody (1/100) was verified with human chondrocytes this antibody did not cross react with bovine chondrocytes. The antibody was diluted in washing buffer (PBS containing 10% blocking buffer DAKO Cytomation X0909). Slides were preblocked in 100% blocking buffer for 1 hour and incubated with the $1^{st}$ antibody overnight. The next day, slides were washed 3 times in washing buffer and incubated with the $2^{nd}$ antibody goat anti-mouse (1:100, DAKO) for 1 hour. Slides were washed 3 times with PBS and staining was visualized with Fluorescent microscope.

Quantitative GAG- and DNA Assay

Micromass cultures for quantitative analysis of GAG's and cell number were washed with PBS and frozen o/n at –80° C. Subsequently they were digested with 1 mg/ml proteinase K (SIGMA-Aldrich) in Tris/EDTA buffer (pH7.6) containing 18.5 μg/ml iodoacetamide and 1 μg/ml pepstatin A (SIGMA-Aldrich) for >16 hrs at 56° C. GAG content was spectrophotometrically determined with 9-dimethylmethylene blue chloride (DMMB, SIGMA-Aldrich) staining in PBE buffer (14.2 g/l $Na_2HPO_4$ and 3.72 g/l $Na_2EDTA$, pH 6.5) with a micro plate reader (Bio-TEK instruments) at an absorbance of 520 nm. Cell number was determined via quantification of total DNA with CyQuant DNA kit according to the manufacturer description (Molecular probes) and fluorescent plate reader (Perkin-Elmer). The standard curve for the analysis was generated using chondroïtin sulfate A (Sigma).

Results

Figure 1B:
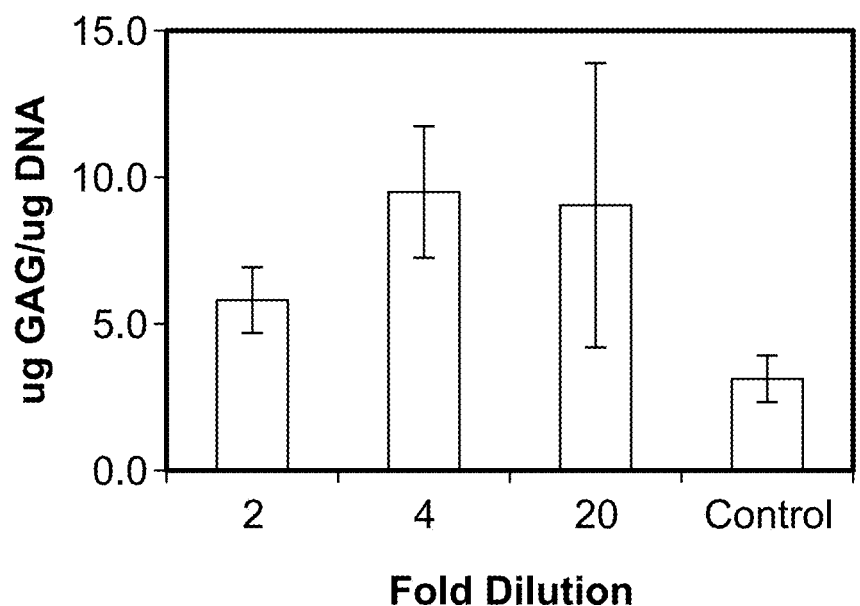
Figure 2:
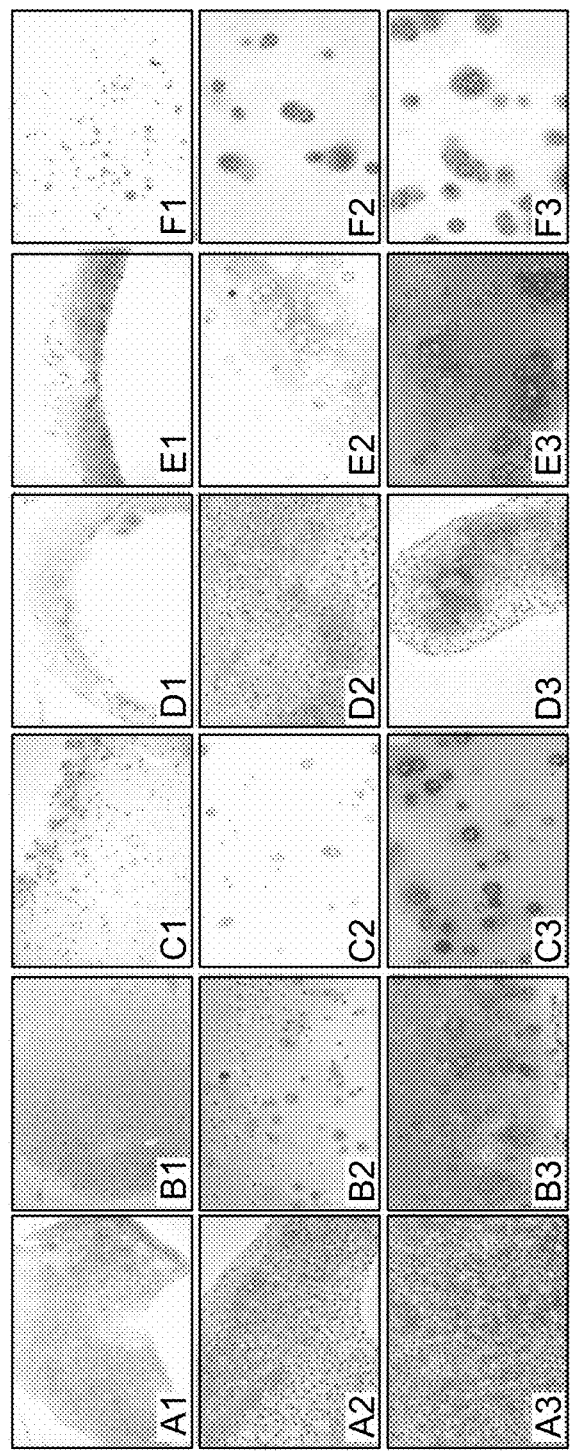
FIG. 2 shows micrographs of primary chondrocytes in micromass culture as explained in detail in the Example. The micrographs show an overview (40×) and detailed (200×)

As can be seen from FIG. 1 and Table 1, when the isolated cells were cultured in gel culture they produce more GAG per unit DNA when they are spaced further apart. Increasing the distance between the cells by either lowering the amount of cells per volume of gel or by increasing the volume of gel at constant cell level, results in a higher production of GAG on a per cell basis.

The invention claimed is:

1. A method to repair a cartilage defect in a mammalian subject which method consists of
   implanting into a cartilage defect in said subject a matrix gel comprising primary chondrocytes, said primary chondrocytes having been isolated from a cartilage sample and mixed with a matrix gel or
   implanting into said defect said matrix gel containing said primary chondrocytes loaded on a scaffold;
   wherein the primary chondrocyte density in the matrix gel is less than 3 million cells/ml.

2. The method of claim 1, wherein said matrix gel comprising primary chondrocytes is essentially free of chondrons.

3. The method of claim 1, wherein said matrix gel comprises a fibrin glue, hyaluronic acid, alginate, propylene fumarate-co-ethylene glycol hydrogel, hydroxypropyl methylcellulose hydrogel, collagen mimetic peptide, chitosan, collagen, gelatin, (ethylene glycol)-co-poly(lactic acid) hydrogel, agarose, poloxamers, copolymers of poly(ethylene glycol)-terephthalate (PEGT) and poly(butylene terephthalate) (PBT), or combinations thereof.

4. The method of claim 1, wherein said primary chondrocytes are autologous chondrocytes obtained from an autologous cartilage sample.

5. The method of claim 1, wherein said cartilage sample comprises articular cartilage.

6. The method of claim 1, wherein said mammalian subject has a cartilage disorder which is articular cartilage trauma, meniscus injury, chondrogenesis disorders or arthritis.

7. The method of claim 1 wherein the primary chondrocyte density in the matrix gel is 0.002-1.0 million cells/ml.

8. The method of claim 1 wherein the primary chondrocyte density in the matrix gel is 0.02-0.6 million cells/ml.

* * * * *